United States Patent [19]

Miyazaki et al.

[11] Patent Number: 4,643,170
[45] Date of Patent: Feb. 17, 1987

[54] ENDOSCOPE APPARATUS

[75] Inventors: Atsushi Miyazaki; Yoshikazu Tohjoh, both of Tokyo, Japan

[73] Assignee: Olympus Optical Co., Ltd., Tokyo, Japan

[21] Appl. No.: 802,377

[22] Filed: Nov. 27, 1985

[30] Foreign Application Priority Data

Dec. 5, 1984 [JP] Japan .................................. 59-256820
Dec. 24, 1984 [JP] Japan .................................. 59-272255

[51] Int. Cl.[4] .............................................. A61B 1/06
[52] U.S. Cl. .................................... 128/6; 350/96.26; 358/98
[58] Field of Search .......................... 128/6, 4; 358/98; 350/96.26

[56] References Cited

U.S. PATENT DOCUMENTS 4,074,306 2/1978 Kakinuma et al. ................. 128/6 X
4,491,865 1/1985 Danna et al. ........................ 128/4 X
4,573,450 3/1986 Arakawa ................................. 128/6

Primary Examiner—William H. Grieb

[57] ABSTRACT

An endoscope apparatus includes an insertion section adapted to be inserted into a desired region. A distal end structure is fixed to the distal end of the insertion section. The structure has a support portion on which a solid-state image sensor is mounted to be movable in a direction parallel to a light receiving surface of the sensor. The sensor is pressed against the support portion by a leaf spring, thereby being prevented from moving in a direction perpendicular to the light receiving surface. A connector is fixed to the proximal end of the insertion section and detachably connected to a control unit.

11 Claims, 16 Drawing Figures

F I G. 5
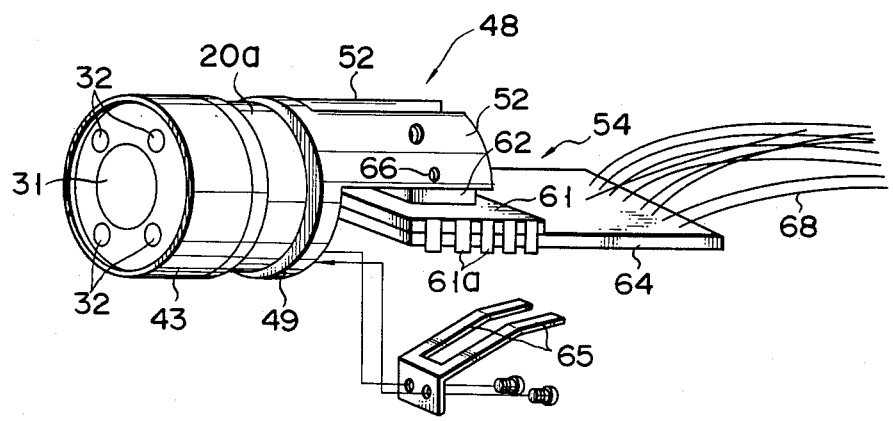
F I G. 6
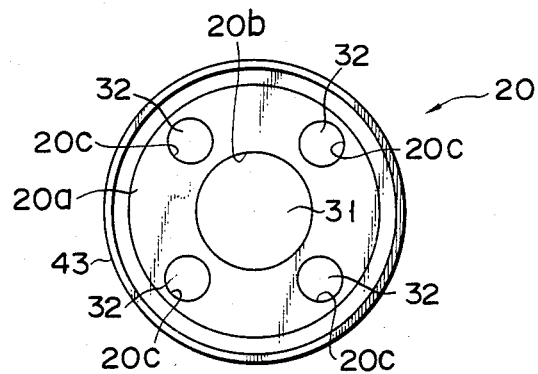
F I G. 7
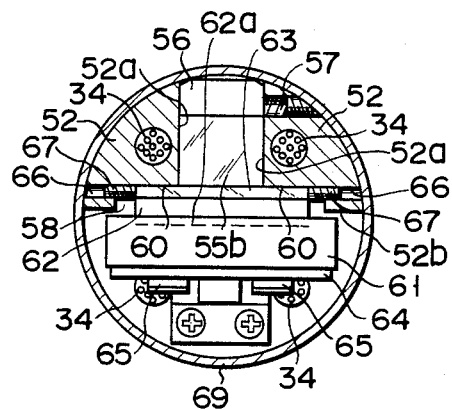

ENDOSCOPE APPARATUS

BACKGROUND OF THE INVENTION

The present invention relates to an endoscope apparatus, and more specifically to an endoscope apparatus in which a solid-state image sensor is used for the observation of an object.

Endoscopes have recently been developed in which a solid-state image sensor is attached to the distal end portion of the insertion section of the endoscope for the observation of an object. In the prior art endoscopes of this type, the image sensor is screwed to a mounting portion of the endoscope, singly or along with a base. When using this mounting method, it is necessary to provide the image sensor or base with a screwing space formed with tapped holes. Thus, the image sensor or base is inevitably bulky, and it is difficult to reduce the size of the distal end portion of the insertion section of the endoscope. Also, it is hard to finely adjust the mounting position of the image sensor at the time of assembling the endoscope.

SUMMARY OF THE INVENTION

The present invention is contrived in consideration of these circumstances, and is intended to provide an endoscope apparatus in which the distal end portion of an endoscope is reduced in size, and the fine adjustment of the mounting position of a solid-state image sensor is easy.

In order to achieve the above object, an endoscope apparatus according to the invention comprises a control unit; a light source; an elongate, flexible insertion section adapted to be inserted into a desired region; a distal end structure attached to the distal end of the insertion section, the distal end structure including a view window, an illumination window, an objective lens system optically connected to the view window and adapted to focus an optical image projected through the view window, and a support portion; a light guide extending from the illumination window through the insertion section to the light source, and adapted to guide a light beam emitted from the light source and radiate the light beam to the outside through the illumination window; a solid-state image sensor having a light receiving surface receiving the optical image focused by the objective lens system and adapted to convert the optical image into an electrical signal and deliver the signal to the drive unit, the image sensor being mounted on the support portion of the distal structure to be movable in a direction parallel to the light receiving surface; urging means for pressing the image sensor against the support portion, thereby preventing the image sensor from moving in a direction perpendicular to the light receiving surface; and an adjusting mechanism for adjusting the position of the image sensor in the direction parallel to the light receiving surface.

BRIEF DESCRIPTION OF THE INVENTION

FIGS. 1 to 12 show an endoscope apparatus according to a first embodiment of the present invention, in which FIG. 1 is a perspective view showing a general configuration of the apparatus, FIG. 2 is a cutaway view of an insertion section, FIG. 3 is a cutaway plan view of a distal end structure, FIG. 4 is a longitudinal sectional view of the distal end structure, FIG. 5 is a perspective view of the distal end structure, FIG. 6 is a front view of the distal end structure, FIG. 7 is a sectional view taken along line VII—VII of FIG. 4, FIG. 8 is a sectional view of a connector, FIG. 9 is a sectional view of the connector taken in a direction different from that of FIG. 8, FIG. 10 is a sectional view taken along line X—X of FIG. 8, and FIGS. 11 and 12 are a plan view and a sectional view, respectively, showing the connector connected to a control unit;

DETAILED DESCRIPTION OF THE PREFERRED EMBODIMENTS

Preferred embodiments of the present invention will now be described in detail with reference to the accompanying drawings.

Figures 1, 2:
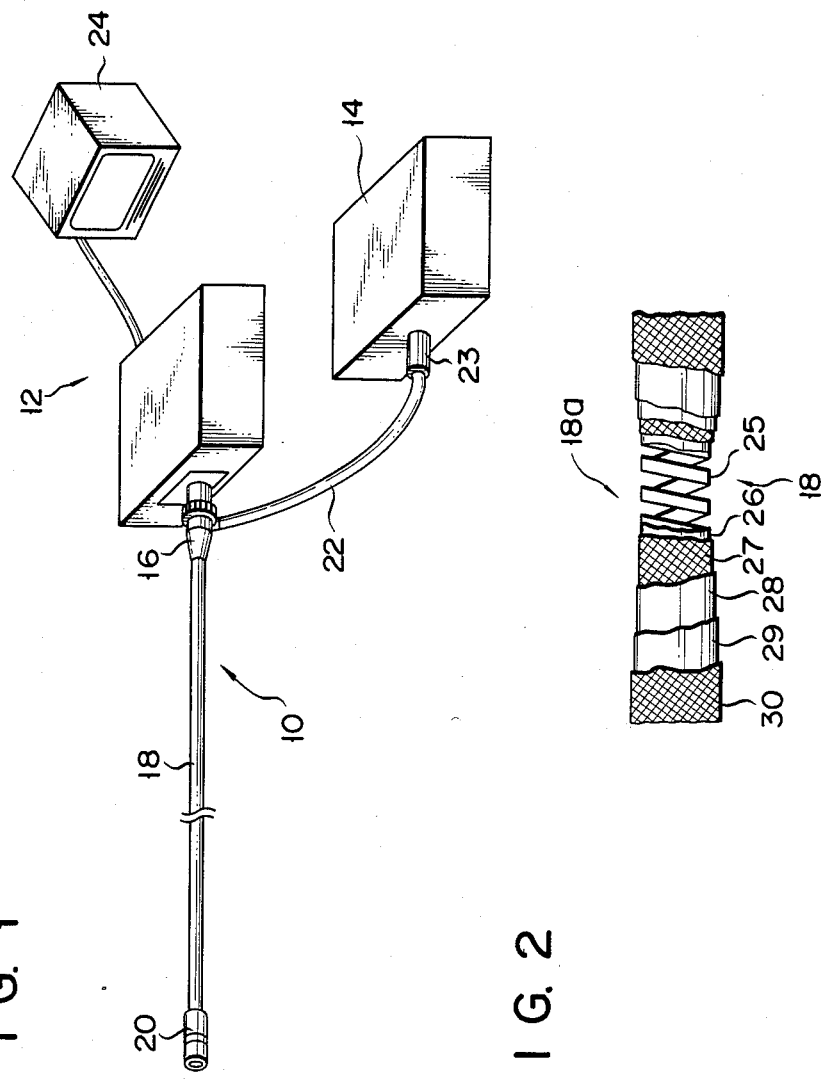
Figure 3:
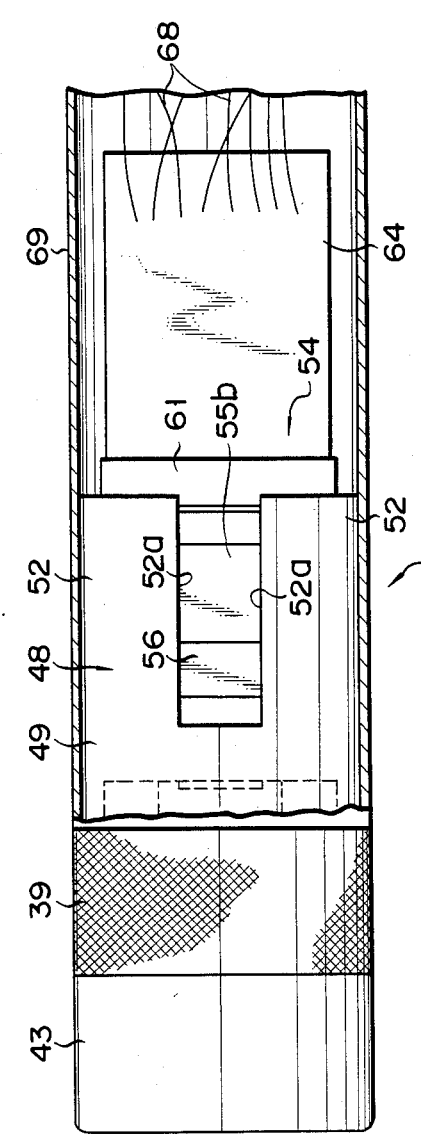
Figure 4:
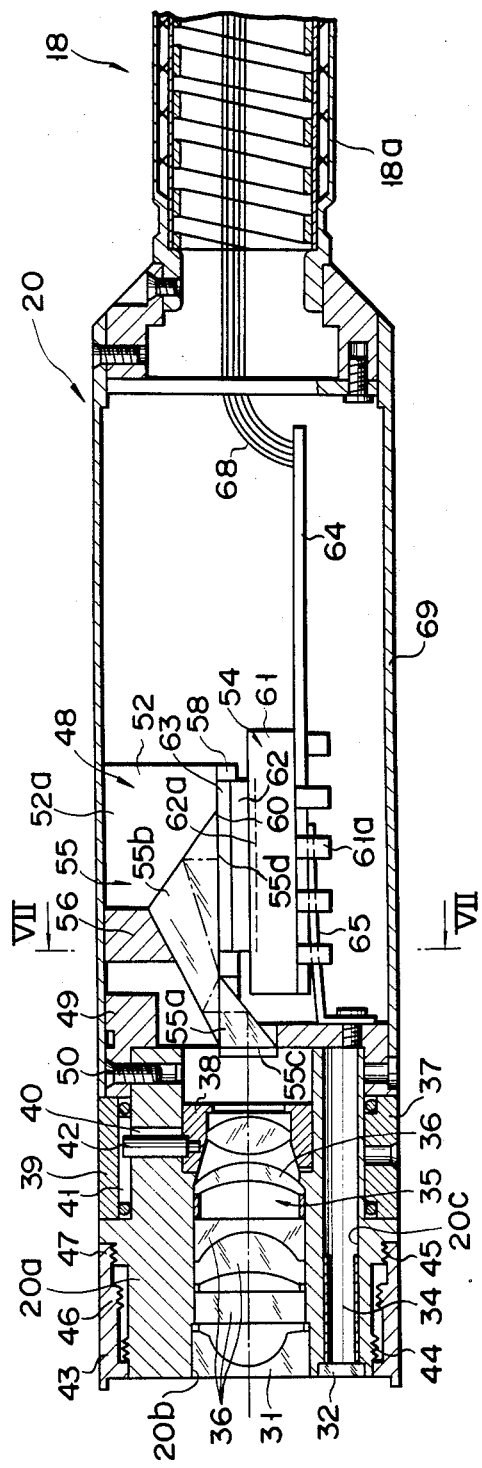

FIG. 1 shows an industrial endoscope apparatus which is used for observation of the interior of jet engines or cables. The apparatus comprises an endoscope 10, and a control unit 12 and a light source unit 14 connected to endoscope 10. Endoscope 10 includes a connector 16 removably connected to control unit 12 and an elongate, flexible insertion section 18 extending from connector 16. A distal end structure 20 is attached to the distal end of insertion section 18. A universal cord 22 extends from connector 16, and is connected to light source unit 14 by means of a connector 23 attached to the extreme end of universal cord 22. Control unit 12 is provided with a monitor 24.

As shown in FIG. 2, insertion section 18 is formed of a flexible tube 18a, which is inserted, along with distal structure 20, into a pipe or the like. Flexible tube 18a includes an elongate spiral flex 25 and a blade 27 covering the outer peripheral surface of flex 25, with a mold release 26 between blade 27 and flex 25. A covering 29 is secured to the outer peripheral surface of blade 27 by an adhesive 28, and a protective blade 30 is put on the outer peripheral surface of covering 29. Protective blade 30 and adhesive 28 may be omitted, as required. The flexibility of flexible tube 18a is maintained by the laminate construction. Tube 18a also has rigidity such that an external force applied thereto can be transmitted along its axial direction. Distal end structure 20 is fixed to the distal end of flexible tube 18a, thus constituting insertion section 18.

As shown in FIGS. 3 to 7, distal end structure 20 has a cylindrical body 20a, which is formed with a coaxial main bore 20b and four sub-bores 20c extending parallel to main bore 20b so as to surround the same. The distal end opening of main bore 20b is closed by a view window 31, and that of each sub-bore 20c by an emission lens 32 as an illumination window. A light guide 34, consisting of a optical fiber bundle, is inserted in each sub-bore 20c and optically connected to each corresponding lens 32. Light guides 34 extend through insertion section 18, connector 16, universal cord 22, and connector 23, and is connected to light source unit 14. Thus, illumination light emitted from light source unit 14 is applied through light guides 34 and lens 32 to a region to be observed.

An objective lens system 35 is disposed in main bore 20b, facing view window 31. Objective lens system 35 includes a plurality of fixed lenses 36 fixed to the inner peripheral surface of main bore 20b, and a focusing lens 37 movable along the axis of main bore 20b or optical axis. Lens 37 is fixed to a lens frame 38 which is disposed in main bore 20b to be movable along its axis. Lens frame 38 is moved by an adjusting ring 39 which is rotatably fitted on the outer peripheral surface of body 20a. Body 20a is formed with a slot 40 which extends in the axial direction of body 20a and communicates with main bore 20b. A spiral groove 41 is formed in the inner peripheral surface of ring 39. A guide pin 42, which extends through slot 40 into groove 41, is fixed to the outer peripheral surface of lens frame 38. Thus, if ring 39 is turned, guide pin 42 is pressed by the side face of groove 41, and moved, together with lens frame 38 and focus lens 37, along the optical axis.

A ring-shaped hood 43 for protecting body 20a is fitted on the outer peripheral surface of the distal end portion of body 20a. Body 20a is formed, on its outer peripheral surface, with a first external threaded portion 44 on the distal end side and a second external threaded portion 45 nearer to the proximal end of body 20a than portion 44. Threaded portion 45 is greater in diameter than first portion 44. Hood 43 is formed, on its inner peripheral surface, with a small-diameter first internal threaded portion 46 to mesh with first external threaded portion 44, and a large-diameter second internal threaded portion 47 to mesh with second external threaded portion 45. When hood 43 is mounted on body 20a, second internal threaded portion 47 passes over first external threaded portion 44 without engaging the same. When first internal threaded portion 46 comes past first external threaded portion 44 after engaging the same, second internal threaded portion 47 reaches second external threaded portion 45. If second internal threaded portion 47 is then screwed on second external threaded portion 45, hood 43 is fixed on body 20a. If second internal threaded portion 47 is disengaged from second external threaded portion 45, first internal threaded portion 46 will be caught by first external threaded portion 44. In this case, therefore, hood 43 is prevented from immediately coming off body 20a.

A support member 48 for supporting a solid-state image sensor (mentioned later) is fixed to the proximal end portion of body 20a. Support member 48 includes a cylindrical portion 49, which is fitted on the proximal end portion of body 20a and fixed by means of a screw 50. A pair of support blocks 52 protrude parallel to each other from cylindrical portion 49, along the axis of body 20a. Opposite faces 52a of support blocks 52 are flat and parallel to each other. Each support block 52 has a lower surface 52b which extends at right angles to face 52a. The respective lower surfaces 52b of support blocks 52 are flush with each other. A solid-state image sensor 54 is opposed to lower surfaces 52b. A covering tube 69 is fixed on the outer peripheral surface of support member 48. The proximal end of covering tube 69 is coupled to the distal end of flexible tube 18a.

A rectangular mounting recess 58 is formed in lower surface 52b of each support block 52. The bottom faces of recesses 58 constitute a datum plane 60. Solid-state image sensor 54 includes a package 61 and a light receiving surface 62a in package 61. A plate like glass cover 63 is fixed on the upper surface of package 61 through a support frame 62 and parallel to light receiving surface 62a. The length and width of glass cover 63 are smaller than those of datum plane 60 of mounting recesses 58. Package 61 is mounted on a printed board 64. Package 61 is fixed and electrically connected to printed board 64 by inwardly bending a plurality of connecting pins 61a which extend from package 61, and then soldering them to printed board 64. A number of lead wires 68 extend from printed board 64 to connector 16, passing through flexible tube 18a.

Solid-state image sensor 54 is arranged so that the upper surface of glass cover 63 is elastically pressed against the bottom faces of mounting recesses 58 or datum plane 60 by a leaf spring 65, as an elastic member, which is screwed to cylindrical portion 49 of support member 48. Thus, glass cover 63 can slide on datum plane 60. In other words, image sensor 54 is movable in a direction parallel to light receiving surface 62a. Each support block 52 is formed with a tapped hole 66 bored through the lateral wall of each corresponding mounting recess 58. An adjusting screw 67 is screwed in each tapped hole 66. The ends of screws 67 engage their corresponding side edges of glass cover 63 of image sensor 54, thereby regulating the position of sensor 54. Thus, the position of sensor 54 can be adjusted by advancing or retreating adjusting screws 67. After the sensor position is adjusted in this manner, glass cover 63 is fixed to datum place 60 of support member 48 by means of an adhesive agent. In consideration of the replacement of image sensor 54, a silicone-based material may be used for the adhesive agent for the ease of separation.

An optical prism system 55, including first and second triangular prisms 55a and 55b coupled to each other, is disposed in a slit defined between faces 52a of support blocks 52. Prisms 55a and 55b are fitted relatively tight in the slit, and can slide along faces 52a. First prism 55a has an incidence surface 55c facing focusing lens 37 of objective lens system 35, while second prism 55b has a radiation surface 55d opposed to glass cover 63 of image sensor 54. A mask is bonded to radiation surface 55d so as to be in contact with glass cover 63. A retaining member 56 is fixed to second prism 55b, located between faces 52a. Optical prism system 55 is moved within the slit between faces 52a by retaining member 56, to be adjusted in position relative to objective lens system 35 and image sensor 54. After the positioning, retaining member 56 is fixed to support blocks 52 by means of screws 57 therein.

An optical image transmitted through objective lens system 35 is projected into first prism 55a through incidence surface 55c, reflected by first prism 55a, and then landed on second prism 55b. Thereafter, the image is emitted from radiation surface 55d of second prism 55b to be incident on light receiving surface 62a of solid-state image sensor 54, passing through glass cover 63. Image sensor 54 changes the received optical image into an electrical signal, which is transmitted through lead wires 68 to control unit 12. Control unit 12 includes a video processing circuit (not shown). The signal delivered from sensor 54 is converted into an image by the video processing circuit, and the image is then projected on monitor 24.

Distal end structure 20 with the above-mentioned construction is assembled in the following manner. First, optical prism system 55 is disposed between faces 52a of support blocks 52. Then, optical system 55 is axially moved by means of retaining member 56 for focusing objective lens system 35. After the focus adjustment, retaining member 56 is fixed to support blocks 52 by means of screws 57. Thereafter, the position of solid-state image sensor 54 is finely adjusted by means of adjusting screws 67. Finally, the adhesive agent is applied between support member 48 and image sensor 54 to fix the same.

Figure 8:
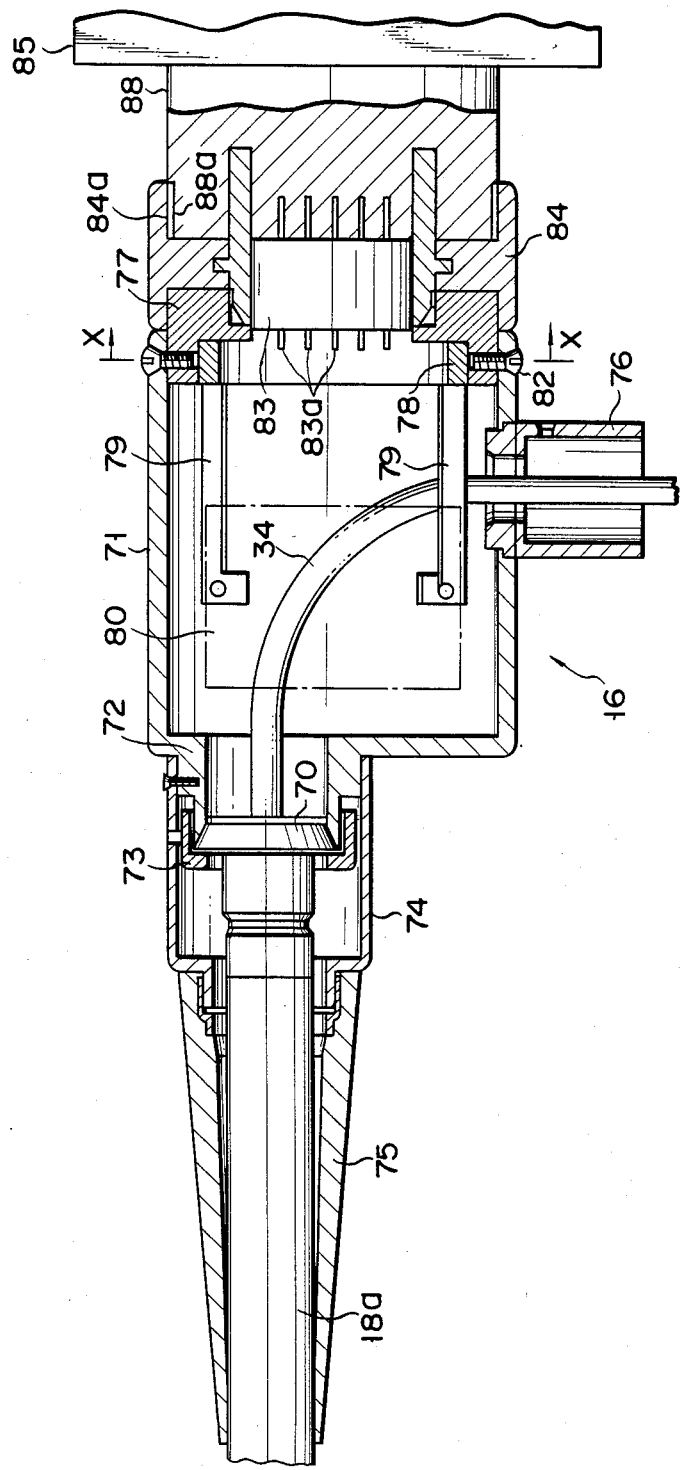
Figure 9:
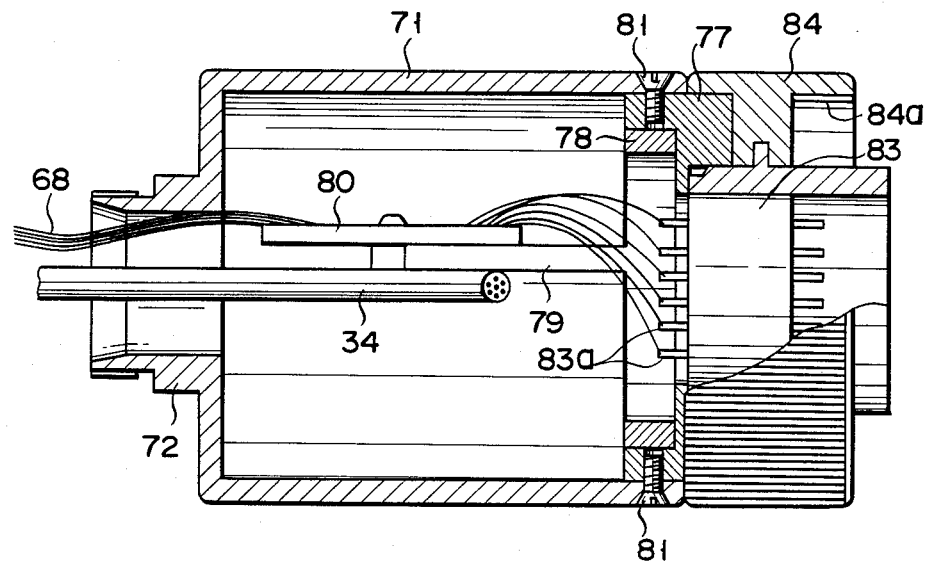

As shown in FIGS. 8 and 9, a mouthpiece 70 having a tapered outer peripheral surface is fixed to the proximal end of flexible tube 18a. Mouthpiece 70 is fitted to a connecting pipe 72 protruding from the forward end of a cylindrical shell 71, and is held in position by a clamp ring 73. An outer pipe 74 is screwed to the outer periphery of connecting pipe 72, covering mouthpiece 70 and the proximal end portion of flexible tube 18a. Also, outer pipe 74 is coupled to a reinforcing tube 75 which is fitted on the proximal end portion of flexible tube 18a. A connecting mouthpiece 76 protrudes radially outward from the outer peripheral surface of shell 71. Universal cord 22 is connected to mouthpiece 76.

Figure 10:
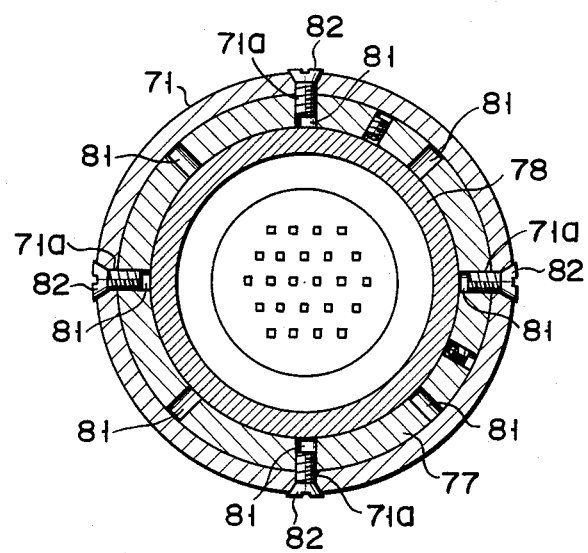

A fixed ring 77 is rotatably fitted in the proximal end portion of shell 71. A support ring 78 is coaxially fitted in fixed ring 77. A pair of parallel support arms 79 projects from support ring 78 into shell 71. A connecting base 80 is supported inside shell 71 by support arms 79. Lead wires 68, which extend from image sensor 54 to pass through flexible tube 18a, are connected to connecting base 80. Connecting base 80 is disposed parallel to a plane which contains the respective centers of mouthpiece 70 of flexible tube 18a and connecting mouthpiece 76. As shown in FIG. 10, four through holes 71a are formed in the proximal end portion of the wall of shell 71, arranged circumferentially at regular intervals. Moreover, eight tapped holes 81 are bored through the wall of fixed ring 77, arranged circumferentially at regular intervals. After shell 71 is rotated relatively to fixed ring 77 so that connecting base 80 is located in the aforesaid position, screws 82 are screwed individually into those tapped holes 81 through holes 71a which face tapped holes 81, thereby fixing ring 77 to shell 71. A columnar connecting plug 83 is coaxially fixed to fixed ring 77, protruding rearward from shell 71. Connecting pins 83a of connecting plug 83 are connected to connecting base 80 by means of lead wires 85. A coupling ring 84 is rotatably fitted on the outer peripheral surface of connecting plug 83. A threaded portion 84a is formed on the inner peripheral surface of coupling ring 84, and is adapted to mate with a receptacle 85 (mentioned later) of control unit 12.

Figure 11:
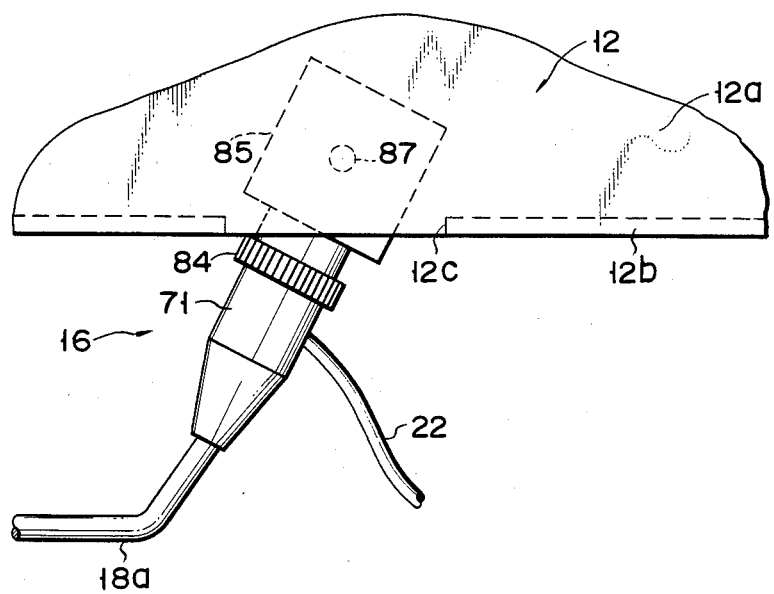
Figure 12:
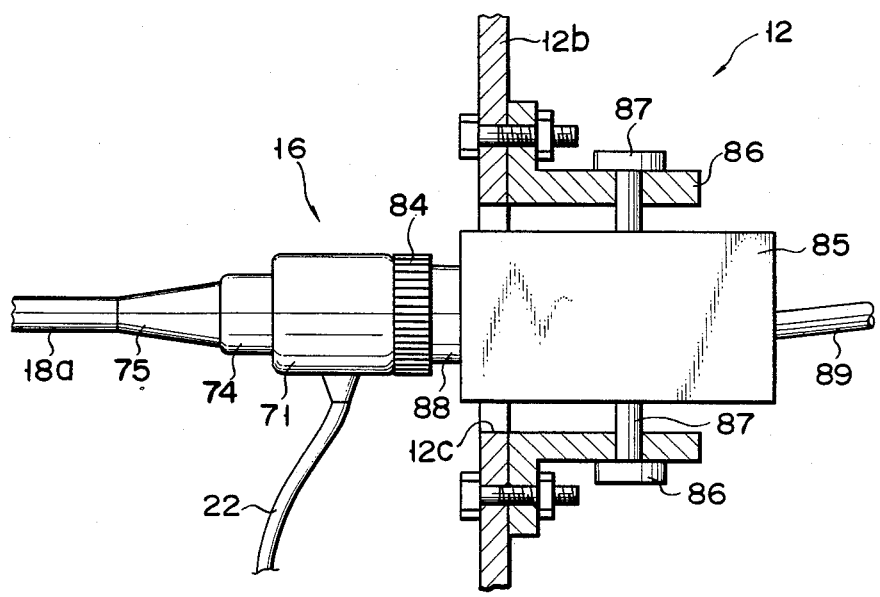

As shown in FIGS. 9, 11 and 12, connector 16, constructed in this manner, is detachably connected to control unit 12. Control unit 12 has a box-shaped housing 12a, and an opening 12c is formed in a front plate 12b of housing 12a. A pair of brackets 86 are fixed to the inside of front plate 12b, facing each other across opening 12c. Receptacle 85, in the shape of a rectangular prism, is disposed between brackets 86. Receptacle 85 is supported on brackets 86 by means of pivots 87 so as to be rockable especially within a horizontal plane. Receptacle 85 includes a socket member 88 which projects outward from housing 12a through opening 12c. A threaded portion 88a is formed on the outer peripheral surface of socket member 88. Connector 16 is connected to control unit 12 by fitting connecting plug 83 to socket member 88 and screwing threaded portion 84a of coupling ring 84 onto threaded portion 88a of socket member 88. Receptacle 85 is connected, by means of a cable 89, to a processing unit, such as the video processing circuit (not shown) in housing 12a. Thus, solid-state image sensor 54 in endoscope 10 is electrically connected various devices in control unit 12 by connecting connector 16 to receptacle 85.

In using the endoscope apparatus constructed in this manner, connector 16 of endoscope 10 is first connected to receptacle 85 of control unit 12, and connector 23 at the distal end of universal cord 22 is connected to light source unit 14. In this state, insertion section 18 of endoscope 10 is inserted into the desired region to be observed, and the image of the region is projected on monitor 24 for observation.

In the endoscope apparatus, endoscope 10 is not provided with an operating section as is required by a prior art endoscope, and connector 16 at the proximal end of insertion section 18 is connected directly to control unit 12. Therefore, insertion section 18 can easily be manually inserted without interfering with the operating section. Receptacle 85 of control unit 12, which is connected with connector 16, is rockable in the horizontal direction and adapted to follow the movement of insertion section 18. Thus, handling of insertion section 18 is facilitated additionally. Moreover, since connectors 16 and 23 are detachably connected to control unit 12 and light source unit 14, respectively, endoscope 10 can be removed from the units when it is to be carried about.

In the endoscope apparatus described above, solid-state image sensor 54 is pressed against datum plane 60 of support member 48 by means of leaf spring 65, and is held so as to be movable in a direction parallel to light receiving surface 62a. It is therefore unnecessary to provide image sensor 54 itself, or printed board 64 supporting the same, with tapped holes for fixing or the like, so that sensor 54 and hence the distal portion of insertion section 18 can be reduced in size. In assembling endoscope 10, moreover, the position of sensor 54 can be finely adjusted with ease.

It is to be understood that the present invention is not limited to the embodiment described above, and that various changes and modifications may be effected therein by one skilled in the art without departing from the scope or spirit of the invention. For example, the elastic member for pressing image sensor 54 against support member 52 is not limited to a leaf spring, and may alternatively be rubber.

Figure 13:
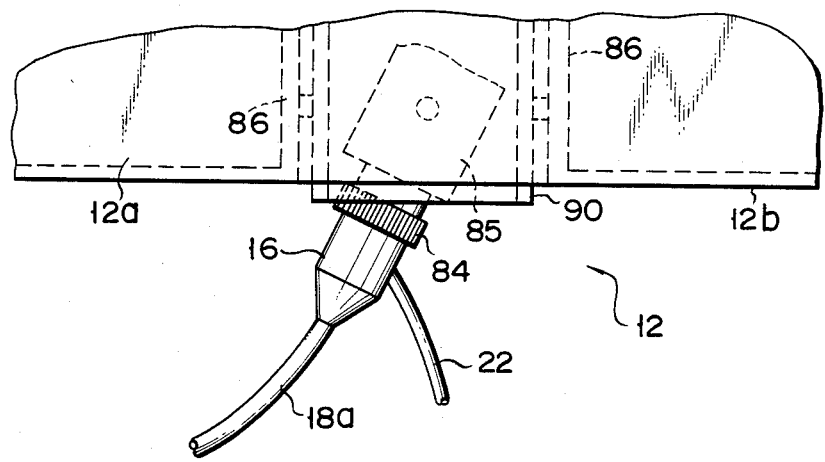
FIGS. 13 and 14 are a plan view and an exploded perspective view, respectively, illustrating the connection between connector and control unit according to a second embodiment of the invention.
Figure 14:
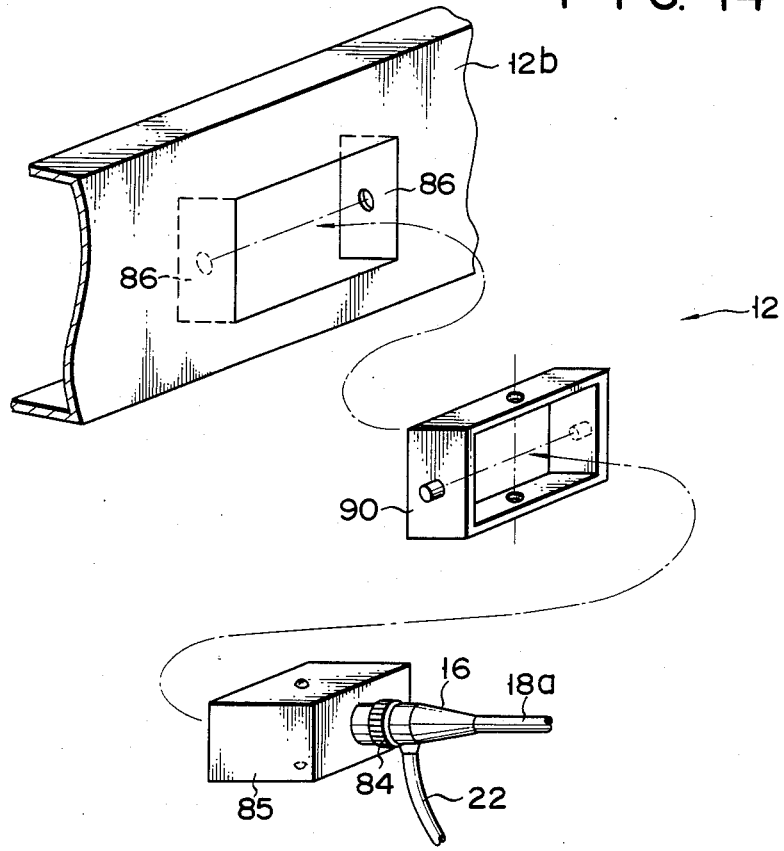

FIGS. 13 and 14 show a second embodiment of the present invention. According to this embodiment, receptacle 85 of control unit 12 is supported by a support frame 90 to be rockable around vertical axis. Support frame 90 is supported to be rockable around horizontal axis, by brackets 86 which are fixed to housing 12a of control unit 12.

In the second embodiment, therefore, receptacle 85 and connector 16 connected thereto can be rocked both horizontally and vertically, further facilitating the insertion of insertion section 18 of endoscope 10.

Figure 15:
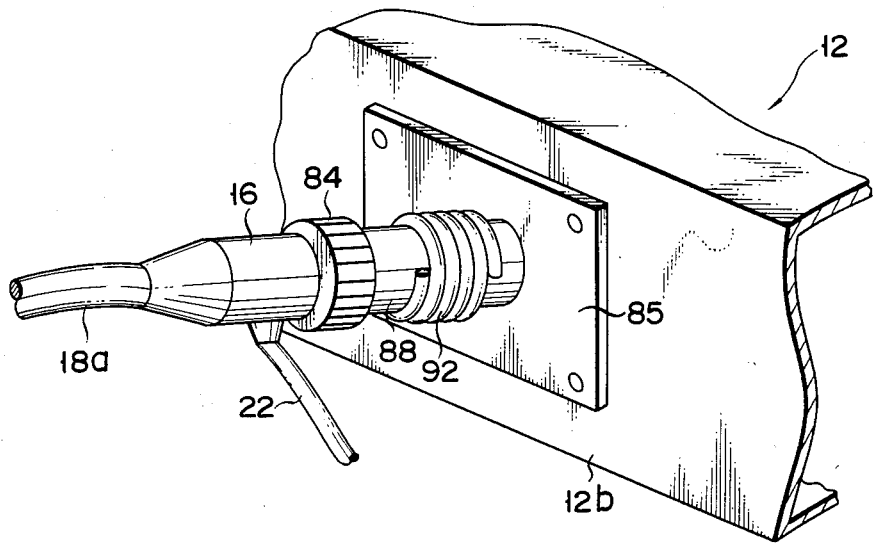
FIG. 15 is a perspective view illustrating the connection between connector and control unit according to a third embodiment of the invention.

According to a third embodiment shown in FIG. 15, receptacle 85 is fixed to housing 12a. In this case, socket member 88 is divided into two blocks, which are coupled together by means of an elastic member, e.g., a coil spring 92. Thus, connector 16 connected to socket member 88 can rock in any direction.

Figure 16:
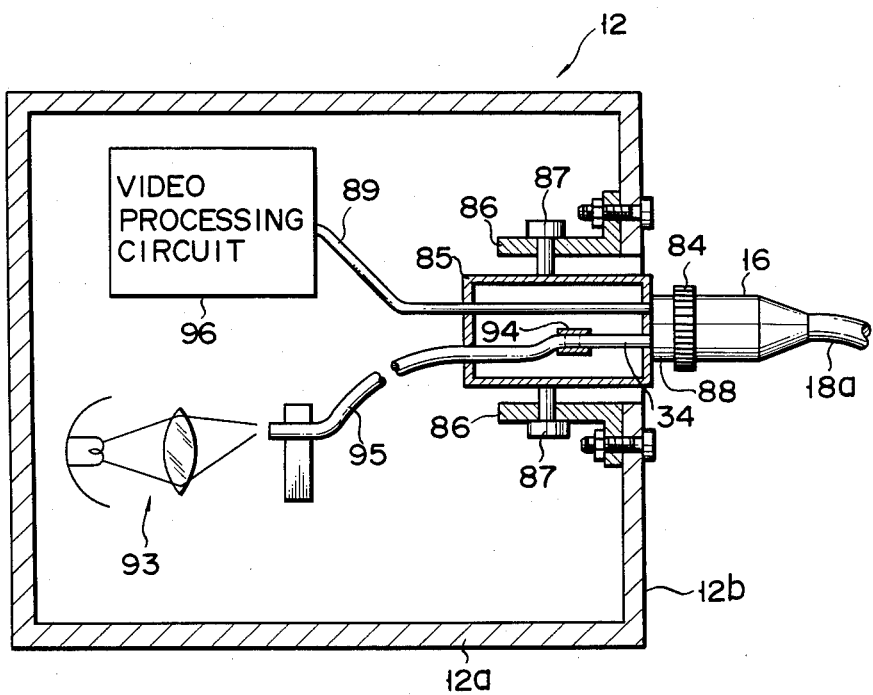
FIG. 16 is a sectional view showing part of an endoscope apparatus according to a fourth embodiment of the invention.

In the foregoing embodiments, light source unit 14 is provided independently of control unit 12. Alternatively, however, the former may be incorporated in the latter, as shown in FIG. 16. In FIG. 16, a light source 93 is disposed in housing 12a of control unit 12. Light guide 34 extending from connector 16 is connected to a connecting ring 94 in receptacle 85. Light source 93 and ring 94 are connected by a relatively long connecting fiber 95 which allows receptacle 85 to rock. Cable 89 extending from receptacle 85 is connected to a video processing circuit 96.

What is claimed is:

1. An endoscope apparatus comprising:
   a control unit;
   a light source;
   an elongate, flexible insertion section adapted to be inserted into a desired region;
   a distal end structure attached to the distal end of the insertion section, said distal end structure including a view window, an illumination window, an objective lens system optically connected to the view window, for focusing an optical image projected through the view window, and a support portion;
   a light guide extending from the illumination window through the insertion section to the light source, for guiding a light beam emitted from the light source and radiating the light beam to the outside through the illumination window;
   a solid-state image sensor having a light receiving surface receiving the optical image focused by the objective lens system, for converting the optical image into an electrical signal and delivering the signal to the control unit, said image sensor being mounted on the support portion of the distal end structure to be movable in a direction parallel to the light receiving surface;
   urging means for pressing the image sensor against the support portion to prevent the image sensor from moving in a direction perpendicular to the light receiving surface; and
   an adjusting mechanism for adjusting the position of the image sensor in the direction parallel to the light receiving surface.

2. The endoscope apparatus according to claim 1, wherein said support portion has a datum plane, said solid-state image sensor has a cover glass facing the light receiving surface and is situated so that the cover glass is slidably in contact with the datum plane, and said urging means urges the image sensor toward the datum plane.

3. The endoscope apparatus according to claim 2, wherein said support portion includes a mounting recess which has a rectangular bottom surface wider than the cover glass and defining the datum plane and at least a pair of opposite lateral faces, and said adjusting mechanism includes at least a pair of adjusting screws screwed into the support portion, each said adjusting screws projecting from each corresponding lateral face and abutting against the image sensor.

4. The endoscope apparatus according to claim 1, wherein said distal end structure includes an optical prism system movably supported by the support portion and optically connecting the objective lens system and the image sensor, said prism system having an incidence surface facing the objective lens system and a radiation surface facing the cover glass of the image sensor.

5. The endoscope apparatus according to claim 1, wherein said urging means is formed of a leaf spring fixed to the support portion.

6. The endoscope apparatus according to claim 1, further comprising a connector attached to the proximal end of the insertion section and adapted to be detachably connected to the control unit.

7. The endoscope apparatus according to claim 6, wherein said control unit includes a housing and a receptacle rockably supported by the housing, and said connector is detachably connected to the receptacle.

8. The endoscope apparatus according to claim 7, wherein said receptacle is rockable around a vertical axis.

9. The endoscope apparatus according to claim 7, wherein said receptacle is rockable around both vertical and horizontal axes.

10. The endoscope apparatus according to claim 6, wherein said control unit includes a housing and a receptacle fixed to the housing, said receptacle having socket means and an elastic member resiliently supporting the socket means, and said connector is detachably connected to the socket means.

11. The endoscope apparatus according to claim 1, wherein said insertion section includes means for transmitting a pressing force exerted on the proximal end of the insertion section to the distal end thereof.

* * * * *